United States Patent
Chang et al.

(10) Patent No.: US 9,050,387 B2
(45) Date of Patent: Jun. 9, 2015

(54) SOUND ABSORBING OSTOMY POUCH

(71) Applicant: HOLLISTER INCORPORATED, Libertyville, IL (US)

(72) Inventors: Moh-Ching Oliver Chang, Lake in the Hills, IL (US); Joel D. Shutt, Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 13/837,867

(22) Filed: Mar. 15, 2013

(65) Prior Publication Data
US 2014/0221950 A1 Aug. 7, 2014

Related U.S. Application Data

(60) Provisional application No. 61/761,981, filed on Feb. 7, 2013.

(51) Int. Cl.
| A61F 5/44 | (2006.01) |
| A61L 28/00 | (2006.01) |
| A61F 5/445 | (2006.01) |

(52) U.S. Cl.
CPC .............. A61L 28/0034 (2013.01); A61F 5/445 (2013.01); A61L 28/0026 (2013.01)

(58) Field of Classification Search
CPC ..................................... A61F 5/44; A61F 5/445
USPC .......................................................... 604/332
See application file for complete search history.

(56) References Cited

U.S. PATENT DOCUMENTS

| 4,855,335 A | 8/1989 | Neperud |
| 5,559,165 A | 9/1996 | Paul |
| 5,567,489 A | 10/1996 | Allen et al. |
| 5,721,025 A * | 2/1998 | Falla et al. ............... 428/35.2 |
| 5,783,269 A | 7/1998 | Heilmann et al. |
| 5,951,533 A | 9/1999 | Freeman |
| 5,968,024 A | 10/1999 | Freeman |
| 6,093,276 A | 7/2000 | Leise, Jr. et al. |
| 6,258,423 B1 | 7/2001 | Giori |
| 6,326,421 B1 | 12/2001 | Lipman |
| 6,387,082 B1 | 5/2002 | Freeman |
| 6,448,303 B1 | 9/2002 | Paul |
| 6,451,883 B1 | 9/2002 | Chen et al. |
| 6,451,912 B1 | 9/2002 | Kelch |
| 6,620,474 B1 | 9/2003 | Regnier et al. |

(Continued)

FOREIGN PATENT DOCUMENTS

| EP | 0787580 A1 | 8/1997 |
| JP | H04357957 A | 12/1992 |

(Continued)

OTHER PUBLICATIONS

International Search Report and Written Opinion in connection with PCT/US2013/051295 dated Oct. 11, 2013.

Primary Examiner — Tatyana Zalukaeva
Assistant Examiner — Guy K Townsend
(74) Attorney, Agent, or Firm — Levenfield Pearlstein, LLC (57) ABSTRACT

An ostomy appliance includes at least one nonwoven layer adhesively attached to at least one of the pouch walls with a sound absorbing adhesive therebetween. The sound absorbing adhesive comprises a vinyl-bond rich triblock copolymer. The ostomy appliance has improved sound absorbing properties to insulate flatus gas noise.

11 Claims, 2 Drawing Sheets

(56) References Cited

U.S. PATENT DOCUMENTS

| | | | |
|---|---|---|---|
| 6,628,474 B1* | 9/2003 | Penman et al. | 360/97.12 |
| 6,685,683 B1 | 2/2004 | Clok et al. | |
| 7,193,002 B2 | 3/2007 | Chen | |
| 7,217,853 B2* | 5/2007 | Kulichikhin et al. | 602/41 |
| 7,255,903 B1* | 8/2007 | Mudar et al. | 428/34.9 |
| 7,270,860 B2 | 9/2007 | Giori | |
| 7,344,568 B2 | 3/2008 | Chen | |
| 7,442,739 B1 | 10/2008 | Hatfield | |
| 7,456,331 B2* | 11/2008 | Kulichikhin et al. | 602/48 |
| 2002/0002363 A1* | 1/2002 | Urakawa et al. | 604/544 |
| 2003/0225356 A1* | 12/2003 | Kulichikhin et al. | 602/54 |
| 2004/0241246 A1 | 12/2004 | Lipman | |
| 2005/0080155 A1 | 4/2005 | Fattman et al. | |
| 2006/0034905 A1 | 2/2006 | Singh et al. | |
| 2006/0135924 A1 | 6/2006 | Luizzi | |
| 2006/0155025 A1 | 7/2006 | Arai et al. | |
| 2007/0051376 A1* | 3/2007 | Kulichikhin et al. | 128/894 |
| 2007/0078197 A1 | 4/2007 | Samuelsen | |
| 2007/0215271 A1* | 9/2007 | McClintic | 156/247 |
| 2007/0237916 A1 | 10/2007 | Rasmussen et al. | |
| 2008/0161492 A1* | 7/2008 | Cleary et al. | 525/50 |
| 2008/0227886 A1 | 9/2008 | Cheney et al. | |
| 2009/0069764 A1 | 3/2009 | Burlot et al. | |
| 2009/0076186 A1 | 3/2009 | Lassalle | |
| 2009/0317614 A1* | 12/2009 | Nilsen et al. | 428/219 |
| 2010/0028411 A1 | 2/2010 | Kawamura et al. | |
| 2010/0121290 A1 | 5/2010 | Rasmussen et al. | |
| 2010/0326598 A1 | 12/2010 | Atwater | |
| 2011/0130698 A1 | 6/2011 | Kutsukake et al. | |
| 2011/0162782 A1 | 7/2011 | Goubard | |
| 2011/0306677 A1 | 12/2011 | Kataoka | |
| 2012/0109033 A1 | 5/2012 | Horstmann et al. | |

FOREIGN PATENT DOCUMENTS

| | | |
|---|---|---|
| WO | 2007076864 A1 | 7/2007 |
| WO | 2008097443 A1 | 8/2008 |
| WO | 2011062829 A1 | 5/2011 |
| WO | 2011157278 A1 | 12/2011 |
| WO | 2012027884 A1 | 3/2012 |

* cited by examiner

SOUND ABSORBING OSTOMY POUCH

CROSS-REFERENCE TO RELATED APPLICATION DATA

This application claims the benefit of priority of Provisional U.S. Patent Application Ser. No. 61/761,981, filed Feb. 7, 2013 entitled, "SOUND ABSORBING OSTOMY POUCH."

BACKGROUND

The present disclosure relates to ostomy appliances, and more particularly to an ostomy pouch made using a sound absorbing laminate including a sound absorbing adhesive.

Ostomy appliances for collecting body waste, such as ostomy pouches, are used by patients who have had surgery such as a colostomy, ileostomy, or urostomy. When body waste is released from a stoma, flatus gas is often released together with the waste. The flatus gas passing through the stoma can cause a vibratory transient in body tissue, which is uncontrollable by the patient. Such release of the flatus gas from the stoma can accompany indiscreet noise, which can cause embarrassment to the patient.

Ostomy pouches comprising a quiet film to reduce noise produced by ostomy pouches, for example, plastic crackling sound made by the ostomy pouch when a user moves around, have been developed. Examples of such a quiet film include multilayer films disclosed in Giori, U.S. Pat. No. 7,270,860, which is assigned to the assignee of the present application and incorporated herein in its entirety by reference. However, these quiet films could be improved upon, to better insulate the flatus noise to prevent embarrassment.

Chang et al., PCT Application No. PCT/US12/71953, which is assigned to the assignee or the present application and incorporated herein in its entirety by reference, discloses sound absorbing films, sound absorbing nonwovens, laminates thereof, and ostomy pouches made using such sound absorbing materials.

Because of the inherent severe medical, social, and personal concerns related to the need for use of an ostomy appliance, improvements in ostomy appliances are desired. Any appreciable improvement in such ostomy appliances to provide greater discretion and privacy is of great importance in the quality of life of the increasing number of ostomy patients. The present disclosure provides improved ostomy appliances according to various embodiments to enhance sound insulating properties of such ostomy appliances.

BRIEF SUMMARY

A sound absorbing adhesive formulated with a vinyl-bond rich triblock copolymer and an ostomy appliance including the same are provided according to various embodiments of the present disclosure. The sound absorbing adhesive can be used to laminate a nonwoven layer to a pouch wall to insulate flatus gas noise.

In one aspect, a sound absorbing ostomy pouch is provided. The sound absorbing ostomy pouch includes a first wall, a second wall, and a first nonwoven layer adhesively attached to the first wall by a sound absorbing adhesive therebetween. A second nonwoven layer can also be adhesively attached to the second wall. The first wall and the second wall are sealed along their peripheral edges to define a cavity for collecting body waste. The sound absorbing adhesive includes a vinyl-bond rich triblock copolymer. Preferably, the vinyl-bond rich triblock copolymer is a non-hydrogenated vinyl-bond rich styrene-isoprene-styrene block copolymer or a hydrogenated vinyl-bond rich styrene-isoprene-styrene block copolymer.

The sound absorbing adhesive may be formulated to include about 2 weight percentage (wt. %) to about 50 wt. % of a non-hydrogenated vinyl-bond rich styrene-isoprene-styrene block copolymer or a hydrogenated vinyl-bond rich styrene-isoprene-styrene block copolymer. Preferably, the sound absorbing adhesive includes about 5 wt. % to about 40 wt. % of the non-hydrogenated vinyl-bond rich styrene-isoprene-styrene block copolymer or the hydrogenated vinyl-bond rich styrene-isoprene-styrene block copolymer. Further, the sound absorbing adhesive can include a tackifier and an end block modifying resin. Preferably, the sound absorbing adhesive has a tangent delta value of greater than about 1.0 at 25° C. between 150 Hz and 2,000 Hz frequencies.

In one embodiment, the sound absorbing adhesive is formulated with about 60 wt. % to about 80 wt. % of at least one tackifier, about 0 to about 15 wt. % of an end block modifying resin, about 5 wt. % to about 40 wt. % of a non-hydrogenated vinyl-bond rich styrene-isoprene-styrene block copolymer, and about 0 to about 2 wt. % of all antioxidant.

In another embodiment, the sound absorbing adhesive is formulated with about 60 wt. % to about 80 wt. % of at least one tackifier, about 5 wt. % to about 40 wt. % of a hydrogenated vinyl-bond rich styrene-isoprene-styrene block copolymer, and about 0 to about 2 wt. % of an antioxidant.

In some embodiments, the sound absorbing ostomy pouch further includes a second nonwoven layer adhesively attached to the second wall by the sound absorbing adhesive therebetween. Preferably, at least one of the first and second nonwoven layers is formed of a sound absorbing nonwoven including fibers comprising a vinyl-bond rich triblock copolymer. Further, at least one of the first wall and the second wall can be formed of a sound absorbing film including a vinyl-bond rich triblock copolymer.

In one preferred embodiment, the first wall is formed from a multilayer film having a thickness of about 1 mil to about 3 mil. The first nonwoven layer is formed from a sound absorbing nonwoven including a vinyl-bond rich triblock copolymer, and having a basis weight of about 40 gsm and a thickness of about 8 mil. The sound absorbing adhesive having a thickness of about 1 mil to about 3 mil is arranged between the first wall and the first nonwoven layer.

In some sound absorbing ostomy pouch embodiments including a second nonwoven layer, the second wall can be formed from a multilayer film having a thickness of about 1 mil to about 3 mil, and the second nonwoven layer can be formed from a sound absorbing nonwoven including a vinyl-bond rich triblock copolymer, and having a basis weight of about 40 gsm and a thickness of about 8 mil. The sound absorbing adhesive having a thickness of about 1 mil to about 3 mil is arranged between the second wall and the second nonwoven layer.

Further, the multilayer film can be a five-layer film including a seal layer, an inner layer, a tie layer, a barrier layer, and an adhesive contact layer.

In another aspect, a sound absorbing adhesive including a vinyl-bond rich triblock copolymer and a tackifier is provided.

The sound absorbing adhesive can be formulated with about 2 wt. % to about 50 wt. % vinyl-bond rich triblock copolymer. Preferably, the sound absorbing adhesive is formulated with about 5 wt. % to about 40 wt. % of a non-hydrogenated vinyl-bond rich styrene-isoprene-styrene block copolymer or a hydrogenated vinyl-bond rich styrene-isoprene-styrene block copolymer.

In one embodiment, the sound absorbing adhesive is formulated with about 14 wt. % of a cycloaliphatic hydrocarbon tackifier, about 61 wt. % of a hydrocarbon tackifier, about 14 wt. % of an alpha-methyl styrene end block modifying resin, about 5 wt. % to about 40 wt. % of a non-hydrogenated vinyl-bond rich styrene-isoprene-styrene block copolymer, and about 1 wt. % of a phenolic antioxidant.

In another embodiment, the sound absorbing adhesive is formulated with about 5 wt. % to about 20 wt. % of a cycloaliphatic hydrocarbon tackifier, about 50 wt. % to about 70 wt. % of a hydrocarbon tackifier, about 5 wt. % to about 40 wt. % of a hydrogenated vinyl-bond rich styrene-isoprene-styrene block copolymer, and about 0 to about 2 wt. % of a phenolic primary antioxidant.

Preferably, the sound absorbing adhesive has a tan delta of greater than about 1.0 at 25° C. between 150 Hz and 2,000 Hz frequencies, a viscosity of less than about 8,000 cP at 165° C., and G' of less than about 120,000 Pa at 25° C.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 1:
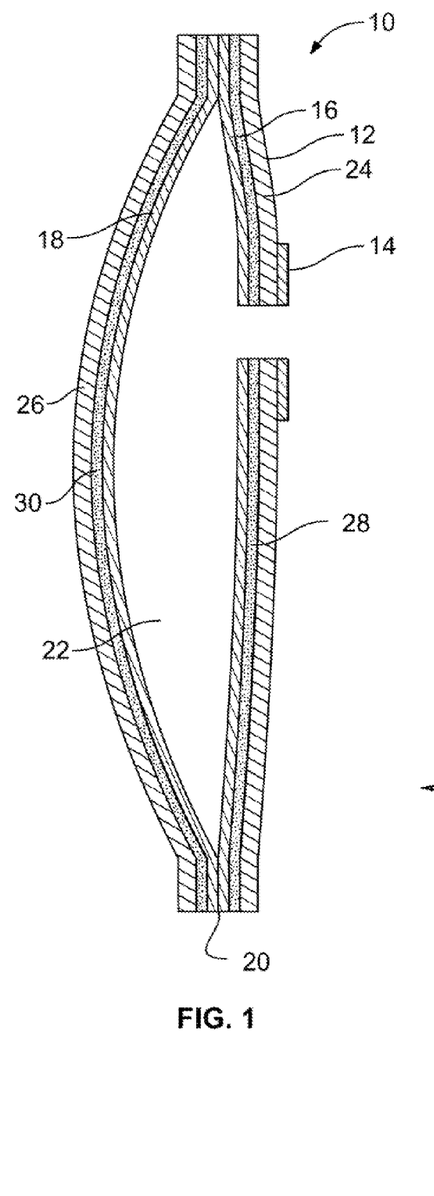
FIG. 1 is a cross-sectional illustration of an ostomy appliance including a pouch and a seal barrier in accordance with an embodiment of the present disclosure.

FIG. 1 is a cross-sectional illustration of a one-piece ostomy appliance 10 according to an embodiment. The ostomy appliance generally includes a pouch 12 and a seal barrier 14. The pouch 12 includes first and second opposing walls 16, 18, which are sealed around peripheral edges 20 thereof by heat sealing or by any other suitable means to define a cavity 22 therebetween. The pouch 12 also includes a first nonwoven layer 24 adhesively attached to the first wall 16 by a first adhesive 28 therebetween, and a second nonwoven layer 26 adhesively attached to the second wall 18 by a second adhesive 30 therebetween. Each of the first and second adhesive layers 28, 30 is formed of a sound absorbing adhesive including a vinyl-bond rich triblock copolymer.

The first and second walls 16, 18 are formed from a suitable polymeric film, and each of the walls can be formed from the same film or different films. The films can be a single layer film or a multilayer film, such as a multilayer film including an odor barrier layer used in commercially available ostomy pouches.

Preferably, each of the first and second walls 16, 18 is formed of a relatively thin multilayer film to allow for a thicker layer of the sound absorbing adhesive 28, 30. In one embodiment, the total thickness of a body side laminate including the first wall 16, the first sound absorbing adhesive 28 and the first nonwoven layer 24 is about 10.4 mil to about 12.4 mil, in which the first wall 16 is formed of a multilayer film having a thickness of about 1 mil to about 2 mil, the first sound absorbing adhesive has a thickness of about 1.4 mil to about 2.4 mil, and the first nonwoven layer has a thickness of about 8 mil. Similarly, the total thickness of an outer laminate including the second wall 18, the second sound absorbing adhesive 30, and the second nonwoven layer 26 is about 10.4 mil to about 12.4 mil, in which the second wall 18 is formed of a multilayer film having a thickness of about 1 mil to about 2 mil, the second sound absorbing adhesive has a thickness of about 1.4 mil to about 2.4 mil, and the second nonwoven layer has a thickness of about 8 mil.

Figure 2:
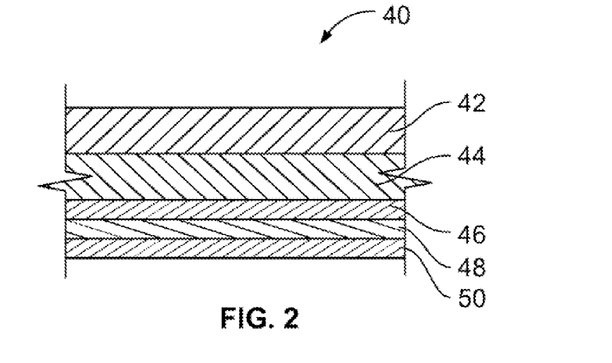
FIG. 2 is a cross-sectional illustration of a multilayer film for pouch walls according to an embodiment.

In this embodiment, each of the first and second walls 16, 18 is formed of a five-layer film having odor barrier properties and a thickness of about 25 μm to about 50 μm (about 1 mil to about 2 mil). FIG. 2 shows a cross sectional view of a live-layer film embodiment suitable for the first and second walls 16, 18. The five-layer film 40 includes a seal layer 42, an inner layer 44, a tie layer 46, a barrier layer 48, and an adhesive contact layer 50, and has a seal layer/inner layer/tie layer/barrier layer/adhesive contact layer construction. Preferably, the film 40 is relatively thin, for example having a thickness of about 40 μm, in which the seal layer 42 has a thickness of about 20 μm, the inner layer 44 has a thickness of about 8 μm, the tie layer 46 has a thickness of about 4 μm, the barrier layer 48 has a thickness of about 4 μm, and the adhesive contact layer 50 has a thickness of about 4 μm.

The seal layer 42 may be formed of a material having suitable heat sealability, such that the seal layers can be heat sealed to form a pouch. Suitable materials for the seal layer 42 include, for example, copolymers of ethylene with vinyl esters, such as vinyl acetate copolymer (EVA) and copolymers of ethylene methyl acrylate (EMA). EVA copolymers contain about 10 percent by weight (wt. %) to 35 wt. % vinyl acetate and more preferably, about 18 percent vinyl acetate, by weight of the copolymer. One exemplary material is available from ExxonMobil as product Escorene® Ultra FL00218. Such a material has a melting point temperature of 86° C. and a Shore A hardness of about 91. EVA is known to exhibit the necessary characteristics for joining to another EVA member, as by heat sealing, to provide an air-tight, liquid-tight seal at the joint or seal. EVA materials can be blended to facilitate formation and film extrusion. For example, an EVA blend can have about 98 wt. % EVA with about 2 wt. % anti-block and slip additives, in an EVA carrier. One suitable additive is available from A. Schulman Inc., as Polybatch® SAB-1982VA.

EMA copolymers include about 10 to about 35 wt. % of methyl acrylate and preferably about 18.5 wt. % to about 30 wt. % methyl acrylate, of the copolymer. Such EMA copolymers typically have melting point temperatures of about 85° C. to 87° C. and a Shore A hardness of about 73 and Shore D hardness of about 20 to 25. Suitable materials are available from Arkema Inc. as Lotryl®18AM02 and front DuPont as Elvaloy®1330AC. The EMA resins can also be blended with anti-block and slip additives in an EVA carrier. One suitable material for blending is the aforementioned Polybatch® SAB-1982VA. Such a blend can have, for example EMA at about 98 wt. %, with about 2 wt. % Polybatch® SAB-1982VA anti-block and slip additive.

Other suitable materials for the seal layer include polymer blends comprising EVA and EMA. Examples include, but are not limited to, a blend of EVA copolymer (Escorene®FL00218 present at 49 wt. %) and ethylene-propylene copolymer (PP-elastomer, Versify®2200 present at 49 wt. %) with anti-block and slip additives, and a blend of EMA (Elvaloy®1330AC present at 49 wt. %) and PP-elastomer (Versify®2200 present at 49 wt. %) also with anti-block and slip additives. PP-elastomers such as Versify® from Dow, Vistamaxx® from Exxon, and Notio® from Mitsui are also suitable.

In addition to heat sealability, the seal layers 42 can also provide sound absorbing properties to the film 40. In such an embodiment, the seal layer 42 comprises a vinyl-bond rich triblock copolymer, such as Hybrar® from Kuraray Co. Ltd. to enhance mechanical properties and sound absorbing properties of the film 40. For example, the seal layer 42 can be formed from a blend of a non-hydrogenated styrene isoprene copolymer (Hybrar® 5127), a PP-elastomer (Vistamaxx®), and an EMA (Lotryl® 20MA08).

The inner layer 44 is arranged adjacent the seal layer 42, and can impart mechanical (tear) strength to the film 40. Ethylene based polymers, such as ethylene vinyl acetate (EVA) copolymer, ethylene-octene (EO) plastomers, and ethylene-propylene (EP) copolymers (PP-elastomer) are suitable film forming materials for the inner layer. One suitable material is an EVA copolymer having a vinyl acetate content of about 8 wt. % to 30 wt. % and preferably about 10 wt. % to about 25 wt. %, a melting point temperature of about 86° C. and a Shore A hardness of about 91, such as Escorene®FL00218.

Another suitable material is an ethylene octene (EO) plastomer having a melting point temperature of about 95° C. and a specific gravity of about 0.902, such as Exact® 0203 resin available from ExxonMobil Corporation, which has a specific gravity of about 0.88 and a Shore A hardness of about 95. This resin is designed for both monolayer and multilayer co-extruded cast film applications and is suitable in applications that require toughness and heat sealing performance. Typical applications include film for industrial packaging.

Still another suitable resin is an ethylene-propylene copolymer (PP-elastomer) resin that exhibits a low melt flow rate making it suitable for film application and heat sealing. It has a low modulus and thus exhibits low noise characteristics. It has excellent compatibility with polypropylene (PP) and polyethylene (PE). One such material is available from Dow Chemical as Versify®2200. This resin has melting point of about 82° C., a Shore A hardness of 94 and a Shore D hardness of 42. It has a specific gravity of 0.878. Blends of various PP copolymer resins have also been found to be suitable, for example, blends of Versify®2200 and Versify®3400, which is a similar PP copolymer resin, but has a higher melting point of about 97° C., a Shore A hardness of 72 and a Shore D hardness of 22, and a specific gravity of about 0.865. Suitable blends can have ratios of about 50 wt. % of Versify®2200 to about 75 wt. % of Versify®2200 of the blend. PP-elastomers such as Versify® from Dow, Vistamaxx® from Exxon, and Notio® from Mitsui are also suitable.

In some embodiments, the inner layer 44 can also provide sound absorbing properties. In such an embodiment, the inner layer 44 comprises a vinyl-bond rich triblock copolymer, such as Hybrar® to enhance mechanical properties and sound absorbing properties of the film 40. For example, the inner layer 44 can be formed from a blend of a hydrogenated vinyl-bond rich styrene-isoprene-styrene block copolymer (e.g. Hybrar® 7125) and a PP-elastomer (Vistamaxx®).

The tie layer 46 is arranged between the inner layer 44 and the barrier layer 48. The tie layer 46 facilitates adhesion of the barrier layer 48 to the remainder of the film structure. Suitable materials for the tie layer 46 include maleated polyolefins, such as a maleated ethylene methyl acrylate copolymers (EMA) having maleic anhydride present at about 0.3 wt. %, and methyl acrylate present at about 20 wt. % of the resin. One such material is available from Arkema, Inc. as Lotader®4503. In one embodiment, the tie layer 46 is formed from a blend comprising 80 wt. % EMA (Lotryl®18MA02 from Arkema. Inc.) and 20 wt. % maleated compound (Bynel®CXA41E710 from Dupont.)

The barrier layer 48 can be formed of a suitable film having gas barrier properties. Preferably, the barrier layer 48 is formed from a non-chlorine containing polymer that is substantially impermeable to malodor causing compounds typically encountered in ostomy pouches. Such malodor causing compounds can include sulfur containing compounds and indoles. Suitable barrier layer materials include resins such as amorphous polyamide (nylon) resin, and an anhydride-modified olefinic polymer or copolymer, or an epoxy modified olefin polymer or copolymer. In one embodiment, the barrier layer 48 is formed from a blend of an amorphous polyamide, such as Selar® PA3426R from DuPont, and a functionalized rubber blend or compound, such as Lotader® 4720 from Arkema, Inc.

The adhesive contact layer 50 is arranged adjacent the barrier layer, and facilitates adhesion of the film 40 to the sound absorbing adhesive layers 28, 30. The suitable tie layer materials are also suitable for the adhesive contact layer 50. For example, maleated ethylene methyl acrylate copolymers (EMA) having maleic anhydride present at about 0.3 wt. % and methyl acrylate present at about 20 wt. % of the resin (Lotader®4503) can be used to form the adhesive contact layer 50.

Other multilayer films with odor barrier properties having more than five layers or less than five layers can also be used to form one or both of the first and second walls 16, 18. For example, a seven-layer film having a structure ABCDCBA, where A represents seal layers, B represents inner layers, C represents tie layers, and D represents a barrier layer, can be used to form the first wall 16 and/or the second wall 18. A six-layer film including a barrier layer, two tie layers, an inner layer, and two seal layers (e.g. ABCDCA) can also be used to form the first wall and/or the second wall 18. The walls 16, 18 can be formed of the same multilayer film or different multilayer films. In a preferred embodiment, the multilayer films for the first and second walls 16, 18 include at least one layer comprising a vinyl-bond rich triblock copolymer, such as a non-hydrogenated vinyl-bond rich styrene-isoprene-styrene block copolymer, e.g. Hybrar® 5125 and 5127, or hydrogenated vinyl-bond rich styrene-isoprene-styrene block copolymer, e.g. Hybrar® 7125.

Referring back to FIG. 1, the first and second walls 16, 18 are provided with the first and second nonwoven layers 24, 26, respectively, which are attached via the first and second adhesive layers 28, 30, respectively. In this embodiment, each of the first and second adhesive layers 28, 30 is formed of a sound absorbing adhesive comprising a vinyl-bond rich triblock copolymer. Suitable sound absorbing adhesives have high sound absorbing properties, good process coatability, and softness. In preferred embodiments, the sound absorbing adhesive formulation includes about 2 wt. %—about 50 wt. % vinyl-bond rich triblock copolymer, about 45 wt. %—about 85 wt. % tackifier, about 0 wt. %—about 30 wt. % end block modifying resin, about 0 wt. %—about 30 wt. % diluent, and about 0 wt. %—about 3 wt. % antioxidant, and has a tan delta at 25° C., of greater than about 1 between 150 Hz and 2,000 Hz frequencies, a viscosity of less than about 8,000 CP at 165° C., and G' of less than about 120,000 Pa at 25° C.

Suitable vinyl-bond rich triblock copolymers include non-hydrogenated vinyl-bond rich styrene-isoprene-styrene block copolymers, such as Hybrar® 5125 and 5127, and hydrogenated vinyl-bond rich styrene-isoprene-styrene block copolymer, such as Hybrar® 7125 and 7311. Suitable elastomers include diblock copolymers, such as a diblock copolymer based on styrene and ethylene/propylene with a polystyrene content of about 28 wt. % (e.g., Kraton®G1702 from Kraton Polymers), polyisobutylene, polyisoprene, and styrene/butadiene copolymers. Suitable tackifiers include cycloaliphatic hydrocarbon (e.g., Escorez® from Exxon Chemical) and hydrocarbon resins (e.g., Regalite® from Eastman Chemical Company, Wingtack® from Goodyear Chemical). Suitable end block modifying resins include aromatic resins based on mixed C9 petroleum distillation streams, resins based on pure or mixed monomer streams of aromatic monomers such as homo or copolymers of vinyl toluene, styrene, alpha-methyl styrene (e.g., Kristalex® from Eastman Chemical Company), coumarone, and indene. Suitable diluents include polyisoprene and polybutenes (e.g., Indopol® from BP). Suitable antioxidants include typical antioxidants used in rubber based pressure sensitive adhesives, such as high molecular weight hindered phenols and multifunctional phenols such as sulfur and phosphorous-containing phenols.

In some embodiments, the sound absorbing adhesive is formulated including about 5 wt. % to 40 wt. % of a non-hydrogenated vinyl-bond rich styrene-isoprene-styrene block copolymer, such as Hybrar® 5125 and 5127, about 7 wt. % to 23 wt. % of a cycloaliphatic hydrocarbon resin, such as Escorez® 5400, about 57 wt. % to 73 wt. % of liquid tackifying hydrocarbon resin, such as Wingtack®10, and about 11 wt. % to about 16 wt. % of an end block modifying resin, such as Kristalex® 3085.

The sound absorbing adhesive may also be formulated including a hydrogenated vinyl-bond rich styrene-isoprene-styrene block copolymer. For example, a sound absorbing adhesive can be formulated including about 5 wt. % to 40 wt. % of a hydrogenated vinyl-bond rich styrene-isoprene-styrene block copolymer, such as Hybrar® 7125 and 7311, about 5 wt. % to 20 wt. % of a cycloaliphatic hydrocarbon resin, such as Escorez® 5400, about 50 wt. % to 70 wt. % of liquid tackifying hydrocarbon resin, such as Wingtack®10, and about 0 to 2 wt. % of an antioxidant, such as Irganox®1010 from Ciba Specialty Chemicals, Inc.

Each of the walls 16, 18 may be adhesively laminated to the nonwoven layer 24, 26 using the sound absorbing adhesive layer 28, 30 therebetween. The nonwoven layers 24, 26 can be formed of any suitable nonwoven materials such as a nonwoven having a basis weight of about 40 grams per square meter (gsm) of polyethylene fibers. Preferably, at least one of the non-woven layers 24, 26 is formed of a sound absorbing non-woven material. The sound absorbing non-woven material may be formed from fibers comprising a vinyl-bond rich triblock copolymer, such as a non-hydrogenated vinyl-bond rich styrene-isoprene-styrene block copolymer, e.g. Hybrar® 5125 and 5127, or a hydrogenated vinyl-bond rich styrene-isoprene-styrene block copolymer, e.g. Hybrar® 7125.

In one embodiment, the fibers are formed of a blend of a vinyl-bond rich triblock copolymer, and polyethylene (PE) or polypropylene (PP). In another embodiment, the fibers are formed of a blend of a hydrogenated vinyl-bond rich styrene-isoprene-styrene block copolymer, such as Hybrar® 7125, and at least one other polymer. For example, the fibers are formed from a blend of Hybrar® 7125 and a hydrogenated poly(styrene-isoprene-styrene) (SEPS), such as Septon®, which is available from Kuraray Co. Ltd. The Septon® SEPS is distinguishable from Hybrar® 7125 in that the midblock of the Septon® SEPS is a hydrogenated polyisoprene whereas the midblock of Hybrar® 7125 is hydrogenated vinyl-polyisoprene. Surprisingly, test results indicate that the vinyl-bond rich Hybrar® 7125 provides significantly better sound absorbing properties than Septon® SEPS. In another example, the fibers are formed from a blend of a low molecular weight hydrogenated vinyl-bond rich styrene-isoprene-styrene (SEPS) block copolymer, such as HG664 from Kuraray Co. Ltd., a Septon® SEPS block copolymer, and a low molecular weight PP.

In some embodiments, the fibers have a sheath and core structure, in which the core is formed of Hybrar® and the sheath is formed of PE or PP. In such an embodiment, the tacky Hybrar® core is enclosed by the sheath, which is advantageous during manufacturing of non-woven materials from the fibers. The sound absorbing non-woven material can be formed by carding and dry-laying such fibers. Alternatively, the non-woven material can be formed via melt blown or spunbond technologies.

Although the ostomy pouch embodiment of FIG. 1 is provided with a nonwoven layer on both the body side and the outer side of the pouch, in other embodiments, an ostomy pouch may be provided with a nonwoven layer on only one side. For example, the body side wall (i.e. the first wall 16) can be laminated to a nonwoven layer using a sound absorbing adhesive, while the outside wall (i.e. the second wall 18) is free of a nonwoven layer or a sound absorbing adhesive layer. Alternatively, the outside wall can be laminated to a nonwoven layer by a sound absorbing adhesive, while the body side wall is free of a nonwoven layer or a sound absorbing adhesive layer.

Although the embodiment shown in FIG. 1 is a one-piece ostomy appliance with a closed-end pouch, the above discussed multilayer films, sound absorbing adhesives, and sound absorbing nonwovens can be used to make other types of ostomy appliances, such as two-piece ostomy appliances and drainable ostomy pouches.

Examples and Test Results

Six different sample adhesive compositions comprising a non-hydrogenated vinyl-bond rich styrene-isoprene-styrene block copolymer were prepared. A control sample was prepared using a pressure sensitive hot melt adhesive available under the tradename Dermatak® from Henkel. The Dermatak® adhesive comprises high molecular weight triblock and diblock copolymers, a paraffinic white oil, an end block modifying resin, and a cycloaliphatic resin (tackifier), and is typically used in skin contact applications including transdermal drug delivery applications. Dynamic Mechanical Analysis (DMA) was conducted for the samples at an oscillation frequency of 10 rad/s, during which dynamic modulus including storage modulus (G'), loss modulus (G"), and complex modulus (G*) were measured. The dynamic modulus values correlate to viscosity and rigidity of an adhesive. For example, higher the G' value, higher the viscosity and rigidity of an adhesive. Further, tangent delta (Tan Δ) values, which correlate to sound absorbing properties of an adhesive, were also measured. For example, a higher Tan Δ value correlates to a higher sound absorbing property.

Sample adhesive AL-43-73-2 was formulated with 15 parts by weight (PBW) (about 14.2 wt. %) Escorez®5400 (a cycloaliphatic hydrocarbon tackifier), 65PBW (about 61.3 wt. %) Wingtack®10 (a hydrocarbon tackifier), 15PBW (about 14.2 wt. %) Kristalex®3085 (an alpha-methyl styrene end block modifying resin), 10PBW (about 9.4 wt. %) Hybrar®5125 (a non-hydrogenated vinyl-bond rich styrene-isoprene-styrene block copolymer), and 1PBW (about 0.9 wt. %) Irganox®1010 (a phenolic primary antioxidant.)

Sample adhesive AL-43-73-3 was formulated with 15PBW (about 14.2 wt. %) Escorez®5400, 65PBW (about 61.3 wt. %) Wingtack®10, 15PBW (about 14.2 wt. %) Kristalex®3085, 10PBW (about 9.4 wt. %) Hybrar®5127 (a non-hydrogenated vinyl-bond rich styrene-isoprene-styrene block copolymer), and 1PBW (about 0.9 wt. %) Irganox®1010.

Sample adhesive AL-43-73-4 was formulated with 15PBW (about 12.4 wt. %) Escorez®5400, 65PBW (about 53.7 wt. %) Wingtack®10, 15PBW (about 12.4 wt. %) Kristalex®3085, 25PBW (about 20.7 wt. %) Hybrar®5125, and 1PBW (about 0.8 wt. %) Irganox®1010.

Sample adhesive AL-43-73-9 was formulated with 15PBW (about 14.2 wt. %) Escorez®5400, 65PBW (about 61.3 wt. %) Wingtack®10, 15PBW (about 14.2 wt. %) Kristalex®3085, 10PBW (about 9.4 wt. %) Hybrar®5125, and 1PBW (about 0.9 wt. %) Irganox®1010.

Sample adhesive AL-43-73-10 was formulated with 23PBW (about 21.7 wt. %) Escorez®5400, 57PBW (about 53.5 wt. %) Wingtack®10, 15PBW (about 14.2 wt. %) Kristalex®3085, 10PBW (about 9.4 wt. %) Hybrar®5125, and 1PBW (about 0.9 wt. %) Irganox®1010.

Sample adhesive AL-43-73-11 was formulated with 23PBW (about 21.7 wt. %) Escorez®5400, 57PBW (about 53.8 wt. %) Wingtack®10, 15PBW (about 14.2 wt. %) Kristalex®3085, 10PBW (about 9.4 wt. %) Hybrar® 5125, and 1PBW (about 0.9 wt. %) Irganox®1010. The sample adhesive formulations are summarized in Table 1.

ing properties for an ostomy pouch, when compared to the same ostomy pouch made using the control adhesive. Further, although the sample adhesive formulations had higher dynamic modulus values than the control adhesive sample, physical characteristic evaluations of the sample adhesive formulations indicate that these adhesive formulations have sufficient viscosity and rigidity for laminating a nonwoven to a pouch wall.

A sample adhesive composition comprising a hydrogenated vinyl-bond rich styrene-isoprene-styrene block copolymer and a control adhesive sample, which is a typical adhesive formulation for bonding a nonwoven to a film layer, such as those used in disposable diaper applications, were prepared. Dynamic Mechanical Analysis (DMA) was conducted for the samples at an oscillation frequency of 10 rad/s, during which dynamic modulus including storage modulus (G'), loss modulus (G"), and complex modulus (G*), and tangent delta (Tan Δ) values were measured. Further, Tan Δ values between about 150 Hz and 2,000 Hz frequencies, which are important indication of sound absorbing properties in ostomy applications, were also measured.

Sample adhesive 42-40-3 was formulated with about 9.9 wt. % Escorez®5400 (a cycloaliphatic hydrocarbon tackifier), about 59.4 wt. % Wingtack®10 (a hydrocarbon tackifier), about 29.7 wt. % Hybrar®7311 (a hydrogenated vinyl-

TABLE 1

Sample Adhesive Formulations

| ingredients | AL-43-73-2 (wt. %) | AL-43-73-3 (wt. %) | AL-43-73-4 (wt. %) | AL-43-73-9 (wt. %) | AL-43-73-10 (wt. %) | AL-43-73-11 (wt. %) |
|---|---|---|---|---|---|---|
| Escorez ®5400 | 14.2 | 14.2 | 12.4 | 14.2 | 21.7 | 21.7 |
| Wingtack ®10 | 61.3 | 61.3 | 53.7 | 61.3 | 53.8 | 53.8 |
| Kristalex ®3085 | 14.2 | 54.2 | 12.4 | 14.2 | 14.2 | 14.2 |
| Hybrar ®5125 | 9.4 | — | 20.7 | 9.4 | 9.4 | 9.4 |
| Hybrar ®5127 | — | 9.4 | — | — | — | — |
| Irganox ®1010 | 0.9 | 0.9 | 0.8 | 0.9 | 0.9 | 0.9 |

The dynamic nodulus values and tangent delta values are summarized in Table 2.

bond rich styrene-isoprene-styrene block copolymer), and about 1 wt. % Irganox®1010 phenolic primary antioxidant.)

TABLE 2

Dynamic Modulus and Tangent Delta Values

Dynamic Mechanical Analysis at 10 rad/s

| | G' at 25° C. (Pa) | G" at 25° C. (Pa) | G* at 25° C. (Pa) | Tan Δ at 25° C. | Temp(tanΔ peak) (° C.) | Peak Tan Δ |
|---|---|---|---|---|---|---|
| Control | 15,942 | 5,935 | 17,013 | 0.4 | −10.5 | 4.2 |
| AL-43-73-2 | 43,160 | 321,000 | 323,900 | 7.4 | 20.4 | 8.5 |
| AL-43-73-3 | 56,020 | 306,700 | 311,800 | 5.5 | 18.5 | 7.4 |
| AL-43-73-4 | 47,170 | 74,580 | 88,250 | 1.6 | 9.0 | 5.3 |
| AL-43-73-9 | 29,890 | 156,123 | 558,943 | 5.2 | 17.9 | 8.6 |
| AL-43-73-10 | 40,919 | 248,576 | 248,307 | 6.1 | 18.0 | 8.2 |
| AL-43-73-11 | 55,430 | 320,145 | 336,835 | 5.7 | 20.4 | 7.2 |

As can be seen in Table 2, the sample adhesive formulations including a non-hydrogenated vinyl-bond rich styrene-isoprene-styrene block copolymer (i.e. Hybrar® 5125 or Hybrar® 5127) had substantially higher tangent delta values than the control adhesive sample, which were prepared from an adhesive used in some known ostomy pouches to laminate a nonwoven to a pouch wall. The higher tangent values indicate that the adhesive formulations including the non-hydrogenated vinyl-bond rich styrene-isoprene-styrene block copolymer can provide significantly improved sound absorb- Control adhesive sample was formulated with about 59.5 wt. % Eastotac®H100W from Eastman (a tackifier based on hydrogenated hydrocarbon resin), about 20 wt. % Calsol®5550 from Calumet (a naphthenic process oil), about 20 wt. % Kraton®1165 from Kraton (a SIS block copolymer), and about 1 wt. % Irganox®1010. The sample adhesive formulation and the control adhesive formulation are summarized in Table 3.

TABLE 3

Adhesive Sample Formulations

| Ingredients | 42-40-3 (wt. %) | Control (wt. %) |
|---|---|---|
| Escorez ®5400 | 9.9 | |
| Eastotac ®H100W | | 59.5 |
| Calsol ®5550 | | 20 |
| Wingtack ®10 | 59.4 | |
| Kraton ®1165 | | 20 |
| Hybrar ®7311 | 29.7 | |
| Irganox ®1010 | 1 | 0.5 |

The data from Dynamic Mechanical Analysis (DMA) at frequency of 10 rad/s are summarized in Table 4.

TABLE 4

Dynamic Mechanical Analysis Data

| | G' at 23° C. (Pa) | G" at 25° C. (Pa) | G* at 25° C. (Pa) | Tan Δ at 25° C. | Peak Tan Δ |
|---|---|---|---|---|---|
| Control | 1,276,061 | 2,934,472 | 3,200,417 | 2.3 | 3.4 |
| 42-40-3 | 109,600 | 71,043 | 130,613 | 0.7 | 3.6 |

Figure 3:
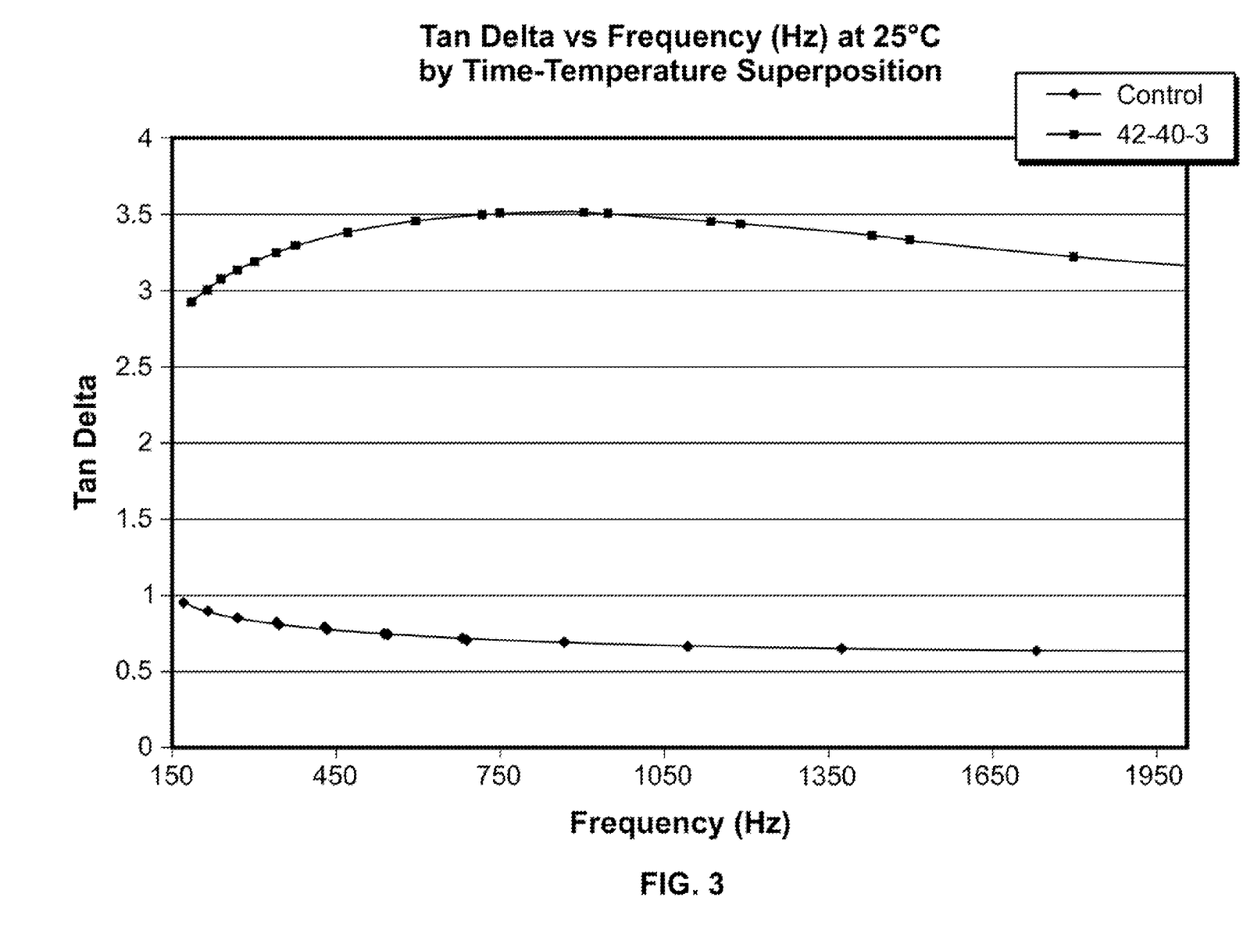
FIG. 3 is a graph showing tangent delta data for a sound absorbing adhesive sample and a control adhesive sample.

FIG. 3 is a graph showing tan Δ values between about 150 Hz and 2,000 Hz. As can be seen in FIG. 3, Sample adhesive 42-40-3 including a hydrogenated vinyl-bond rich styrene-isoprene-styrene block copolymer (i.e. Hybrar® 7311) had substantially higher tangent delta values between 150 Hz and 2,000 Hz frequencies than the control adhesive sample. These higher tangent values indicate that the adhesive formulation including the hydrogenated vinyl-bond rich styrene-isoprene-styrene block copolymer can provide significantly improved sound absorbing properties for an ostomy pouch, when compared to the same ostomy pouch made using the control adhesive. Further, Sample adhesive 42-40-3 had significantly lower dynamic modulus values than the control adhesive sample, indicating that Sample adhesive 42-40-3 is a softer adhesive with a lower viscosity than the control adhesive, which is advantageous for ostomy applications.

In the present disclosure, the words "a" or "an" are to be taken to include both the singular and the plural. Conversely, any reference to plural items shall, where appropriate, include the singular. All of the concentrations noted herein as percentage are percentage by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A sound absorbing ostomy pouch, comprising:
    a first wall,
    a second wall, wherein the first wall and the second wall are sealed along their peripheral edges to define a cavity;
    a first nonwoven layer adhesively attached to the first wall by a sound absorbing adhesive therebetween; and
wherein the sound absorbing adhesive comprises about 60 wt.% to about 80 wt.% of at least one tackifier and about 2 wt.% to about 40 wt.% of a vinyl-bond rich triblock copolymer, wherein the vinyl-bond rich triblock copolymer has a tangent delta peak temperature of greater than about −20° C., and wherein the sound absorbing adhesive has a tangent delta of greater than about 1.0 at 25° C. between 150 Hz and 2,000 Hz frequencies.

2. The sound absorbing ostomy pouch of claim 1, wherein the vinyl-bond rich triblock copolymer is a non-hydrogenated vinyl-bond rich styrene-isoprene-styrene block copolymer or a hydrogenated vinyl-bond rich styrene-isoprene-styrene block copolymer.

3. The sound absorbing ostomy pouch of claim 1, wherein the sound absorbing adhesive further includes an end block modifying resin.

4. The sound absorbing ostomy pouch of claim 1, wherein the sound absorbing adhesive further includes about 0 to about 15 wt.% of an end block modifying resin, and about 0 to about 2 wt.% of an antioxidant, wherein the vinyl-bond rich triblock copolymer is a non-hydrogenated vinyl-bond rich styrene-isoprene-styrene block copolymer.

5. The sound absorbing ostomy pouch of claim 1, wherein the sound absorbing adhesive further includes about 0 to about 2 wt.% of an antioxidant, wherein the vinyl-bond rich triblock copolymer is a hydrogenated vinyl-bond rich styrene-isoprene-styrene block copolymer.

6. The sound absorbing ostomy pouch of claim 1, further including a second nonwoven layer adhesively attached to the second wall by the sound absorbing adhesive therebetween.

7. The sound absorbing ostomy pouch of claim 6, wherein at least one of the first and second nonwoven layers is formed of a sound absorbing nonwoven including fibers comprising a vinyl-bond rich triblock copolymer.

8. The sound absorbing ostomy pouch of claim 1, wherein at least one of the first wall and the second wall is formed of a sound absorbing film including a vinyl-bond rich triblock copolymer.

9. The sound absorbing ostomy pouch of claim 1, wherein the first wall is formed from a multilayer film having a thickness of about 1 mil to about 3 mil, and the sound absorbing adhesive has a thickness of about 1 mil to about 3 mil, and the first nonwoven layer is formed from a sound absorbing nonwoven having a basis weight of about 40gsm and a thickness of about 8 mil, wherein the sound absorbing nonwoven comprises a vinyl-bond rich triblock copolymer.

10. The sound absorbing ostomy pouch of claim 6, wherein the second wall is formed from a multilayer film having a thickness of about 1 mil to about 3 mil, and the sound absorbing adhesive has a thickness of about 1 mil to about 3 mil, and the second nonwoven layer is formed from a sound absorbing nonwoven having a basis weight of about 40gsm and a thickness of about 8 mil, wherein the sound absorbing nonwoven comprises a vinyl-bond rich triblock copolymer.

11. The sound absorbing ostomy pouch of claim 9, wherein the multilayer film is a five-layer film including a seal layer, an inner layer, a tie layer, a barrier layer, and an adhesive contact layer.

* * * * *

UNITED STATES PATENT AND TRADEMARK OFFICE
CERTIFICATE OF CORRECTION

PATENT NO.         : 9,050,387 B2
APPLICATION NO.    : 13/837867
DATED              : June 9, 2015
INVENTOR(S)        : Chang et al.

Page 1 of 1

It is certified that error appears in the above-identified patent and that said Letters Patent is hereby corrected as shown below:

Title Page, item (74) attorney, column 2, line 1, "Levenfield Pearlstein, LLC" to read as --Levenfeld Pearlstein, LLC--.

In the Specification

Column 1, line 35 approx., "or" to read as --of--.

Column 2, line 22 approx., "all" to read as --an--.

Column 9, line 41 approx., "nodulus" to read as --modulus--.

Signed and Sealed this
Twenty-fourth Day of November, 2015

Michelle K. Lee
*Director of the United States Patent and Trademark Office*